(12) United States Patent
Thuemen et al.

(10) Patent No.: US 11,812,929 B2
(45) Date of Patent: Nov. 14, 2023

(54) PLUG CONNECTION FOR A VIDEO ENDOSCOPE, VIDEO ENDOSCOPE AND METHOD FOR PRODUCING A PLUG CONNECTION

(71) Applicant: OLYMPUS WINTER & IBE GMBH, Hamburg (DE)

(72) Inventors: Alrun Thuemen, Hamburg (DE); Sebastian Jungbauer, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 159 days.

(21) Appl. No.: 17/204,238

(22) Filed: Mar. 17, 2021

(65) Prior Publication Data

US 2021/0290044 A1 Sep. 23, 2021

(30) Foreign Application Priority Data

Mar. 18, 2020 (DE) .......................... 102020107492.1

(51) Int. Cl.
*A61B 1/00* (2006.01)
*A61B 1/05* (2006.01)
*H01R 12/77* (2011.01)

(52) U.S. Cl.
CPC ........ *A61B 1/00124* (2013.01); *A61B 1/0011* (2013.01); *A61B 1/00105* (2013.01);
(Continued)

(58) Field of Classification Search
CPC ............ A61B 1/00124; A61B 1/00105; A61B 1/0011; A61B 1/00114; A61B 1/05;
(Continued)

(56) References Cited

U.S. PATENT DOCUMENTS

2015/0065800 A1* 3/2015 Jungbauer .............. A61B 1/051
600/110
2015/0335230 A1* 11/2015 Tomatsu ............ A61B 1/00018
600/109
(Continued)

FOREIGN PATENT DOCUMENTS

CN 105025777 A 11/2015
DE 299 23 887 U1 6/2001
(Continued)

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

A plug connection between distal video and proximal cable units, including: a plug; and a connector inserted into the plug, the plug is a glass cast part arranged at a proximal end of the distal video unit; the connector is arranged at a distal end of the proximal cable unit; the plug is connected to a housing of the distal video unit, has electrical feedthroughs and is connected on a distal side to a first flexboard in the distal video unit and has a connector receptacle; the connector is enclosed in a housing formed to fit the connector receptacle; the connector has a plurality of electrical feedthroughs arranged in accordance with an arrangement of the electrical feedthroughs of the plug; and the electrical feedthroughs are connected proximally to a second flexboard having a planar solder pad structure having solder pads, to which signal and connecting cables are soldered.

12 Claims, 3 Drawing Sheets

(52) U.S. Cl.
CPC ............ *A61B 1/00114* (2013.01); *A61B 1/05* (2013.01); *H01R 12/771* (2013.01); *H01R 2201/12* (2013.01)

(58) Field of Classification Search
CPC .......... A61B 1/04; H01R 12/59; H01R 24/20; H01R 24/66; H01R 43/0256; H01R 43/20; H01R 12/771; H01R 2201/12; H01R 12/778; H01R 13/6215; H01R 24/28; H01R 13/502
See application file for complete search history.

(56) References Cited

U.S. PATENT DOCUMENTS

| | | | | |
|---|---|---|---|---|
| 2018/0006389 A1* | 1/2018 | Wieters | ................ | H01R 12/592 |
| 2020/0280118 A1* | 9/2020 | Vook | ........................ | H01P 5/026 |
| 2021/0267735 A1* | 9/2021 | Galluseder | ................ | A61L 2/18 |

FOREIGN PATENT DOCUMENTS

| | | | | | |
|---|---|---|---|---|---|
| JP | 2001-008885 A | | 1/2001 | | |
| JP | 2001008885 A | * | 1/2001 | ......... | A61B 1/00126 |
| JP | 2006-192202 A | | 7/2006 | | |
| JP | 2007-229085 A | | 9/2007 | | |
| JP | 2015-066287 A | | 4/2015 | | |
| JP | 2016-019749 A | | 2/2016 | | |
| WO | WO 2016/146393 A1 | | 9/2016 | | |
| WO | 2019/103734 A1 | | 5/2019 | | |

* cited by examiner (State of the art)

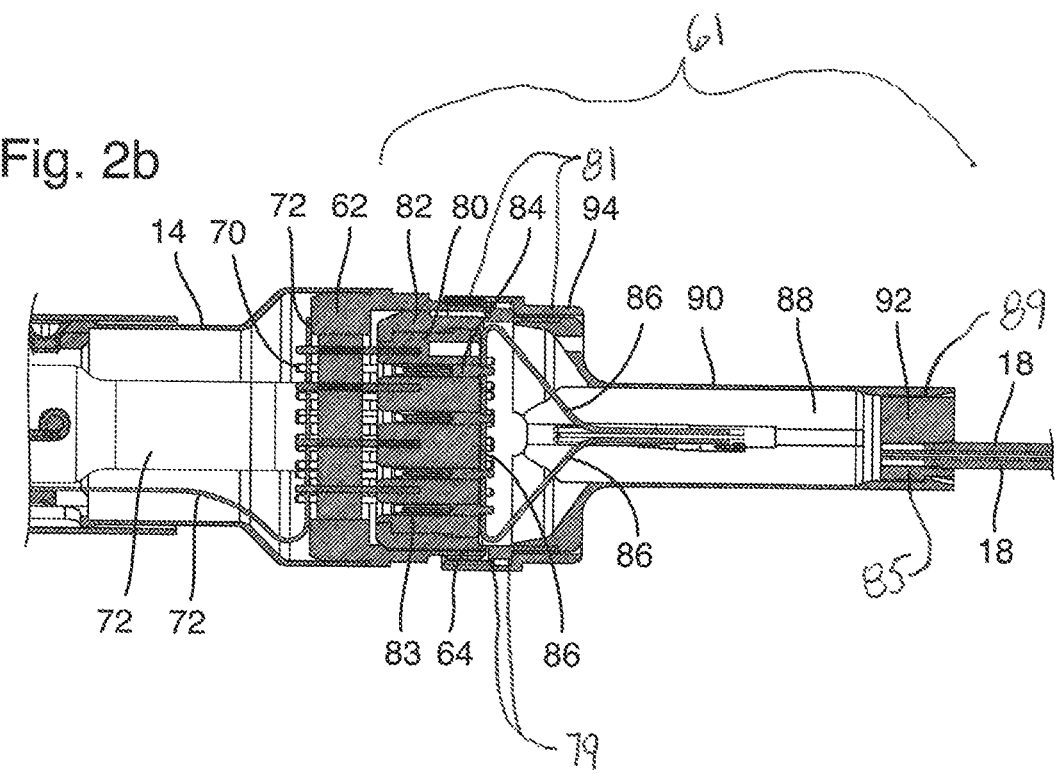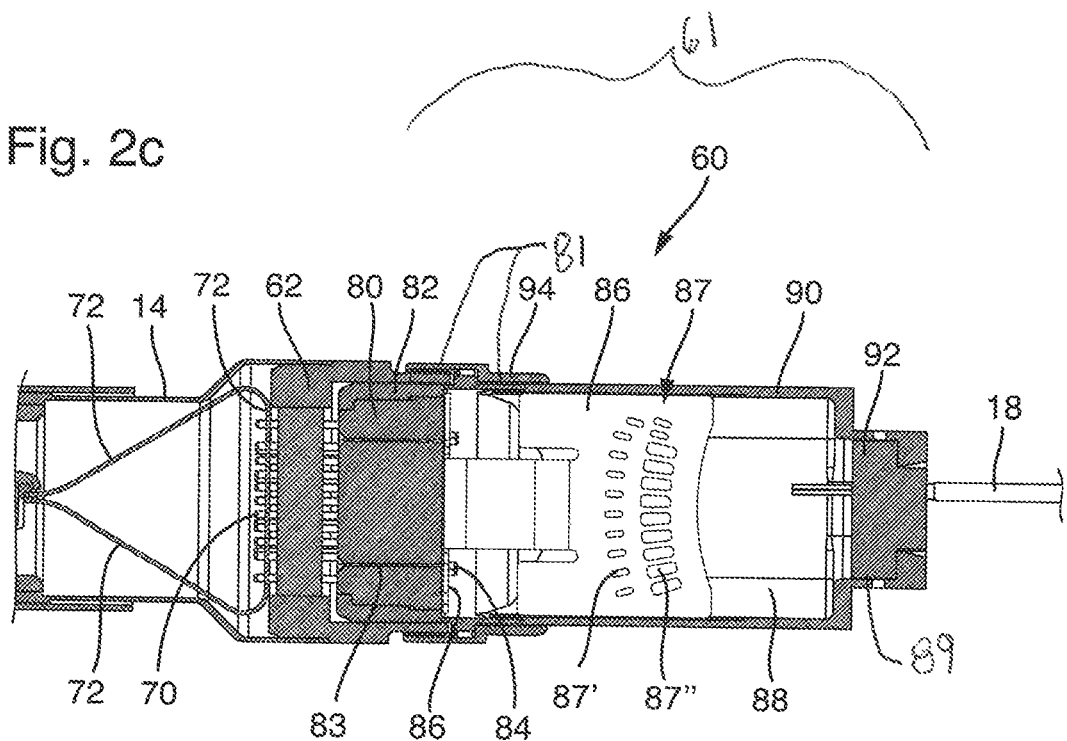

PLUG CONNECTION FOR A VIDEO ENDOSCOPE, VIDEO ENDOSCOPE AND METHOD FOR PRODUCING A PLUG CONNECTION

CROSS-REFERENCE TO RELATED APPLICATION

The present application is based upon and claims the benefit to DE 10 2020 107 492.1 filed on Mar. 18, 2020, the entire contents of which are incorporated herein by reference.

BACKGROUND

Field

The present disclosure relates to a plug connection for a video endoscope for producing a signal connection between a distal video unit and a proximal cable unit of the video endoscope, a corresponding video endoscope as well as a method for producing a corresponding plug connection.

Prior Art

In video endoscopes, there is a plug connection between the distal video unit, also referred to as an R unit, which usually includes for instance the endoscope shaft and the image sensor as well as the read-out electronics thereof, and the proximal cable unit, also referred to as a cable unit, which usually comprises the handle. Said plug connection connects the video lines of the video unit to those of the cable. On the side of the video unit there is a 30-pin plug having a glass casting, an O-ring and a coil spring ring for sealing and securing. Said spring and the O-ring do not always function and are damaged relatively quickly.

The connector on the side of the cable unit is assembled from multiple parts. The cables are manually stripped in a multiple-step process and the outer shield is soldered into a ferrule, i.e., a stopper having passages for the cables. Thereafter, the individual strands are soldered into solder buckets of the connector; to this end, in part, a solder adapter is additionally still required for the thicker strands. Many of the single lines are coaxial cables. The shields thereof are twisted, combined in groups and also soldered in solder buckets. The connector is subsequently pressed into the housing. Thereafter, the inner space is cast with a thick-layer lacquer up to the thread and subsequently the plug having the mount. Lastly, the ferrule is soldered to the lid. The plug connection is then secured with screws and spring rings.

This process of assembling the plug manually is elaborate and prone to errors. The plug does not lend itself easily to connecting, since the plugs can only be pre-aligned with respect to one another optically, and not tactilely. By this, it is not guaranteed that the feedthroughs (pins) engage directly in the base of the counterpart. Furthermore, two screws braced with spring washers are to be tightened, which takes a long time and is prone to errors. Soldering the cables to the solder buckets is difficult since the cables have different line diameters. The shields of the coaxial cables have to be partially twisted to form groups. Said groups can have different thicknesses and also have to be soldered to the buckets. Since the installation space is very small, this soldering process is difficult and prone to errors, resulting in frequent touching-up work. The outer cable shielding is further soldered to the ferrule. Since the latter is round, it can also rotate during assembly. This can cause the already soldered cables inside to twist and thus to shorten. The solderings are thus stressed and possibly pre-damaged, which can lead to early failures during use.

The insecure fixing, uncertain watertightness and large constructional form of the plug are further points that make handling difficult. The spring and the O-ring do not always work or are quickly damaged. The casting only extends up to the thread, as a result of which the cables in the rear part of the connector are not protected. The fastening eyelets or eyes of the plug protrude a great deal and do not permit a narrower handle design.

The electrical signal transmission is not ideal either. In order to be able to attach the inner coaxial lines to the solder buckets of the plug, shielding groups must be created. Furthermore, it is necessary to guide the inner conductors in long arcs. This construction represents a large jump in the transfer impedance of the plug and is unfavorable for fast digital signals.

FIGS. 1a) to 1c) schematically show a known plug connection 20 of a video endoscope 10. The plug connection 20 is sheathed in FIG. 1a), while it is represented in FIGS. 1b) and 1c) in two vertical sections. The section in FIG. 1b) runs through vertically between the two cables, while the sectional plane in FIG. 1c) runs vertically thereto in a plane which runs through the two screws 28, that is to say above the central axis of the substantially cylindrical plug connection 20.

It is shown in FIG. 1a) that the plug connection 20, toward one side, adjoins a distal video unit 12 and, toward the opposite side, adjoins the proximal cable unit 16. The distal video unit 12 is usually arranged in an endoscope shaft of the video endoscope 10, while the proximal part is arranged in a handle of the video endoscope 10. On the distal side, the plug connection 20 is enclosed in a housing 14, on the proximal side in a connector housing 42, which is terminated proximally with a lid 50. The cables 18 lead through a ferrule 52 having openings for the cables 18 into the connector housing 42 of the plug connection 20. For sealing purposes, the ferrule 52 is soldered into the lid 50 and the cables 18 are soldered into the ferrule 52. On the side of the distal video unit 12, a plug 22 is pressed into an extended part of the housing 14 and projects proximally out of said housing 14. In said region, the plug 22 is hollow internally and has a connector receptacle 23, into which the connector 40 is introduced with its connector housing 42. The plug connection is secured by a screw connection to two eyes 26 having an internally threaded bore and two screws 28 having spring washers, wherein the connector housing 42 also has corresponding eyes (without reference numerals), which align with the eyes 26 of the plug 22 which can for example be a 30-pin plug.

The cables 18 can be signal cables for the video signals, but also supply cables for supplying the video unit 12 with electricity, or from other instruments.

In FIG. 1b), a cross-section of the plug connection 20 is shown, which runs through vertically between the two cables 18. The solid plug 22, which can be constructed as a glass casting, is represented centrally on the distal side. In the cross-section shown here, the latter has a U-shape, the base of which points distally and is interspersed with electrical feedthroughs 30 (pins) which are hermetically inset into the glass casting. The electrical feedthroughs 30 project distally from the plug 22 and are connected to a circular base of a flexboard 32 which has conductive tracks as well as solder pads (not shown), at which the feedthroughs 30 are electrically connected to the solder pads or respectively conductive tracks of the flexboard 32. Two arms of the flexboard 32 are bent in with respect to one another and are held together in shape by means of a non-conductive connecting element 34. The distal end of the flexboard 32, which is not shown, can for example be inserted into a corresponding jack (not shown).

The plug 22 has a substantially cylindrical edge pointing proximally, which, in the cross-section shown, represents the arms of the U-shape, and the inner side of which forms a receptacle 23 for the connector 40 of the plug connection 20, which connector forms the connection to the cables 18 proximally. Said connector 40 likewise has a similarly large number of electrical feedthroughs (44) (pins) which are configured on the distal side as hollow pins in receptacles 43 for the feedthroughs 30 and, consequently, establish a secure electrical contact with the electrical feedthroughs 30 of the plug 22 if the connector 40 is inserted into the plug 22.

Producing the connector 40 is an elaborate process. Firstly, the individual signal conductors of the cables 18 are contacted with the connector 40. This is effected by soldering the strands and the shielding fabrics of the signal lines from the cable 18 to the proximally protruding ends of the electrical feedthroughs 44, if applicable supported by solder adapters 46, also referred to as solder buckets. To this end, the cables 18 are manually stripped in a multiple-step process and the outer shield is soldered into the ferrule 52. Thereafter, the individual strands are soldered into the solder buckets of the connector 40, a solder adapter is in part additionally still required for the thicker strands. Many of the single lines are coaxial cables. The shields thereof are twisted and combined in groups and also soldered in solder buckets.

The connector 40 is subsequently pressed into a, in turn, substantially cylindrical connector housing 42 and the inner space is cast with a casting made of a thick-film lacquer up to the thread of a screw connection 54, in order to mechanically and chemically protect the contactings. The internal thread for the screw connection 54 remains excluded from the casting 48. The proximal side of the connector 40 is further protected by a cover disk 45, through which the electrical feedthroughs 44 likewise project. The cover disk 45 is brought into position and held by structures having a complementary shape in the cover disk 45 and the connector 40. Following the hardening of the casting 48, a lid 50 is screwed into the screw connection 54 of the connector housing 42 from proximally and the ferrule 52, through which the cables 18 are guided, is pulled into the outlet opening of the lid 50 and soldered there.

The thus completed connector 40 is inserted into the plug 22 and the plug connection is then secured with two screws 28 having spring washers, which are guided through eyes (without reference numerals) of the connector housing 42 and are screwed into eyes 26 of the plug 22 having an internally threaded bore.

The outer contours of the connector housing 42 coincide with the inner contour of the edge of the plug 22, and the preferably complementary shapes preferably contain complementary structures which guarantee a correct alignment of the connector 40 with regard to the plug 22 and the respective electrical feedthroughs 30, 44 during insertion. A secure seat as well as a hermetic seal are guaranteed by a circumferential O-ring 24 and a coil spring ring 25 which are arranged in circumferential recesses in the edge of the plug 22 and squeeze the connector housing 42. The spring 25 and the O-ring 24 form a weak point since they do not always function and can be damaged relatively quickly.

As represented in FIG. 1c), the plug connection 20, which is produced by inserting the connector 40 into the plug 22, is secured by means of screws 28 which are screwed through an eye of the connector housing 42 and through an eye 26 of the plug 22 each, wherein the eye 26 of the plug has a suitable internal thread for the screw 28. The screw connection having the screws 28 is stabilized by spring washers which introduce a pretension into the screw connection.

SUMMARY

By way of contrast, an object is to provide a plug connection, a video endoscope and a method for producing such a plug connection which overcomes the indicated disadvantages.

Such object can be achieved by a plug connection for a video endoscope for producing a signal connection between a distal video unit and a proximal cable unit of the video endoscope, comprising a plug and a complementary connector which can be inserted into the plug in order to produce and interrupt the signal connection, wherein the plug is formed as a glass cast part and is arranged at a proximal end of the distal video unit and the connector is arranged at a distal end of the proximal cable unit, wherein the plug is connected on its outer side to a housing of the distal video unit, has a plurality of electrical feedthroughs, is connected in an electrically conducting manner on a distal side to a flexboard in the distal video unit and has on its proximal side a connector receptacle configured as a recess for the connector, wherein the connector is enclosed in a connector housing which is formed on its outer side to fit the connector receptacle of the plug in order to become or be received in the connector receptacle of the plug by form-fit and/or by force-fit, wherein the connector has a plurality of electrical feedthroughs which are arranged in accordance with an arrangement of the electrical feedthroughs of the plug, wherein the electrical feedthroughs of the connector are proximally connected to a flexboard which has a planar solder pad structure having solder pads, to which the signal and connecting cables are soldered.

The production of the plug connection can be simplified by the use, on the connector side, of a flexboard having a planar solder pad structure for contacting the cables leading to the video endoscope. Flexboards had hitherto already been deployed for contacting in the video unit. However, the contacting on the side of the cable unit is mechanically highly loaded, which is why the deployment of flexboards had not hitherto been considered.

As previously, the plug connection can be deployed for the video lines of the video endoscope, but also for example for actuator lines and/or heater lines. The contacting of the strands and shields of the cables on the solder pads of the flexboard is substantially easier than hitherto, and the manufacture of the cables is likewise facilitated. In addition, this construction leads to a substantially smaller jump in the transfer impedance than hitherto.

In embodiments, the plug and the connector housing have structures on their outer sides, such as external threads and termination surfaces, which cause the plug connection to be pressed on and fixed by means of screwing on a union nut. This measure results in a compact but secure connection of the plug contact, which also still leaves space for other parts of an endoscope, for example optical fibers or channels.

The connector housing can have, in embodiments, a smaller cross-sectional area in the region of the flexboard than in the region of the connector. This has been made possible by the use of a flexboard having a planar solder pad structure. As the connector housing tapers proximally, the instrument can have a slimmer and more convenient structure overall. At the same time, there is more space in the handle for further parts, for example operating elements or electronics.

The process of producing the connection is advantageously simplified and made secure if the connector receptacle and the connector housing have mutually complementary structures in order to correctly align the connector and the plug with respect to one another.

In embodiments, the connector housing can be terminated by means of a ferrule which fits into a proximal receptacle of the connector housing, said ferrule having lead-throughs for the signal and supply cables, and the signal and supply cables are soldered into the ferrule. A ferrule is understood to be a stopper having through openings for the cables. The ferrule can, for its part, be soldered into the connector housing. These measures ensure a hermetic and mechanically stable lead-through of the cables into the connector housing.

The ferrule and the proximal receptacle of the connector housing can have, in embodiments, shapes which match one another, which prevent a rotation of the ferrule in the proximal receptacle of the connector housing. Such shapes can be rotationally symmetrical. In cross-section, they are for example flattened, angular or leveled. This measure ensures that only one orientation or two orientations rotated by 180° with respect to one another is/are offered, which simplifies the mounting process. Additionally, the signal and supply cables cannot be twisted and shortened by unwanted torsion of the ferrule in the receptacle of the connector housing.

The connector housing can be completely filled up with a casting in embodiments. The complete casting mechanically secures the connection between the cables and the solder pads on the flexboard completely and optimally reduces harmful mechanical stresses of the solder joints and of the cables.

In embodiments, to simplify assembly, the connector housing can be configured in two parts in order to simplify assembly, wherein the connector is fitted into a distal connector housing part and the ferrule is fitted into a proximal connector housing part. The proximal and the distal connector housing parts are or will be connected to form the connector housing, for example by pressing, such as before the connector housing is filled with a casting through a filling opening. The fact that the housing is in two parts means that it is possible to introduce the connector and the ferrule into the respective connector housing part separately from one another such that handling is considerably simplified.

Such object can also be achieved by a video endoscope having a distal video unit and a proximal cable unit as well as a plug connection and described above for producing a signal connection between the distal video unit and the proximal cable unit. The video endoscope, which comprises an embodiment of the plug connection and described above, therefore realizes all of the advantages, characteristics and features described above.

Such object can also be achieved by a method for producing a plug connection and described above for producing a signal connection between a distal video unit and a proximal cable unit of a video endoscope described above, having the following steps:

the flexboard is soldered to the electrical feedthroughs of the connector on a proximal side of the connector,
side surfaces of the flexboard are bent upwards and the connector is pressed into the connector housing,
the signal and connecting cables are soldered to the solder pads of the planar solder pad structure of the flexboard,
the signal and connecting cables are soldered into the ferrule before or after the soldering to the planar solder pad structure,
the connector housing is closed, and
the ferrule is soldered to the connector housing.

The plug contact described above can be produced with this method. It consequently realizes the same advantages, features and characteristics as the other subject-matter discussed above.

In embodiments of the method, the connector housing can be completely filled up with a casting.

Electrical feedthroughs of a plug configured as a glass cast part can be connected at the proximal end of the distal video unit to contact surfaces of a flexboard which is connected to signal and supply cables in the distal video unit, and the plug is inserted into a housing of the distal video unit and is connected to the housing of the distal video unit such that a part of the plug projects proximally out of the housing. Thus, outer contours of the plug can be used for securing, for instance by an external thread for a union nut.

In order to close the connector housing, a proximal connector housing part can be pushed onto or into a distal connector housing part in embodiments and is pressed with the distal connector housing part. Said two-part configuration of the connector housing allows a simple installation of the electrical contactings between the connector and flexboard as well as between the flexboard and cables.

The plug connection can be secured with a union nut such that a fixed and compact securing is realized.

Further features will become evident from the description of embodiments, together with the claims and the appended drawings. Embodiments can fulfill individual features or a combination of multiple features.

BRIEF DESCRIPTION OF THE DRAWINGS

The embodiments will be described below without limiting the general concept of the invention by means of exemplary embodiments with reference to the drawings, wherein reference is expressly made to the drawings regarding all of the details which are not explained in greater detail in the text, wherein.

DETAILED DESCRIPTION

Figure 1A:
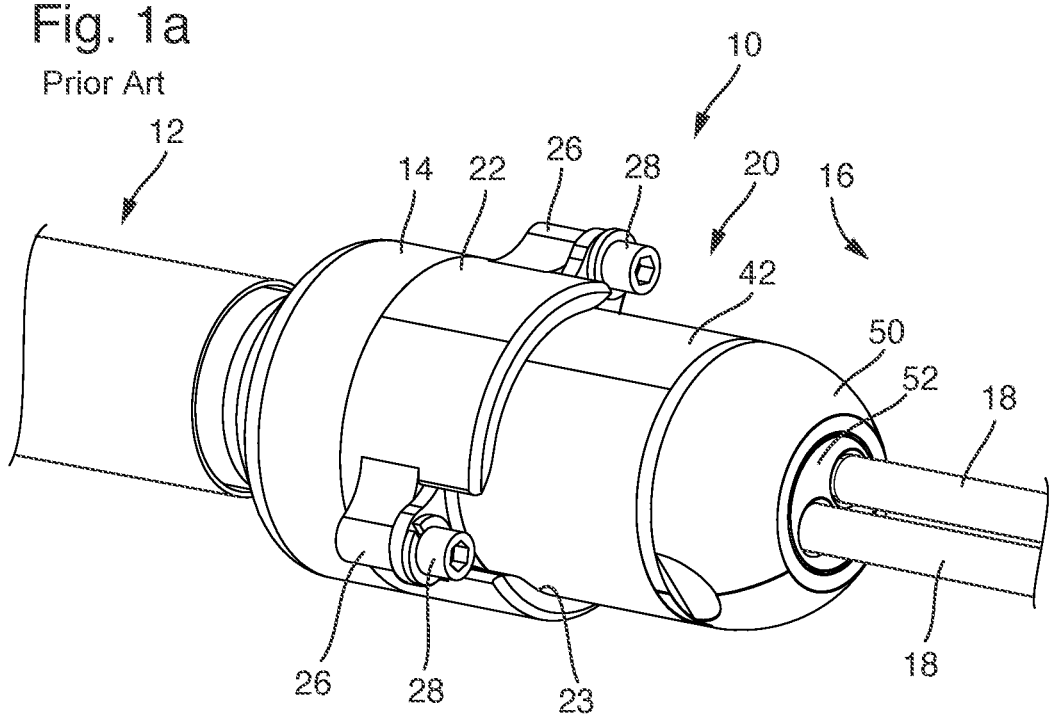
FIGS. 1a)-1c) illustrate a known plug connection for a video endoscope.

In the drawings, the same or similar elements and/or parts are, in each case, provided with the same reference numerals such that they are not introduced again in each case.

Figure 2A:
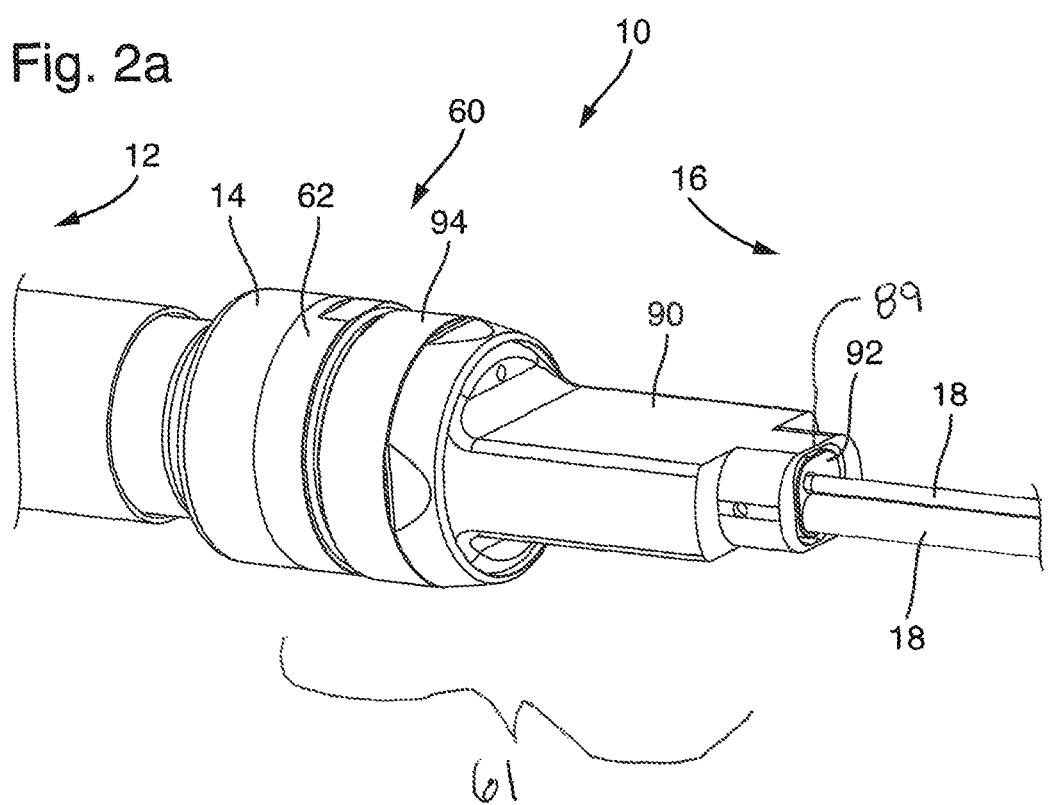
FIG. 2a)-2c) illustrate a plug connection.

A plug connection 60 is schematically shown in FIGS. 2a) to 2c). As can be clearly seen in FIG. 2a), it protrudes to a lesser extent than the known plug connection 20 from FIG. 1a). It can, in turn, be seen on the left side that this part belongs to the distal video unit 12, while the proximal cable unit 16 is provided on the right side. Likewise, a distal housing 14 having the plug part and a proximal connector housing 90 are present, which, however, have a much narrower construction than the connector housing 42 of the known plug connection 20 from FIG. 1a). Instead of a screw connection, the plug connection 60 is secured by means of a union nut 94, which is pitched via a protruding part of the connector housing 90 and is screwed onto an external thread 81 of the plug 62 which is constructed as a glass casting. The plug and the connector housing have structures on their outer sides, such as the external threads and termination surfaces 79, which cause the plug connection to be pressed on and fixed by means of screwing on the union nut 94. A further difference is that the ferrule 92 is not necessarily cylindrical, but can likewise be flattened in accordance with the flattened shape of the proximal end of the housing 90 such that the cables 18 cannot twist with respect to the connector housing 90 and the components arranged therein.

Sections through the plug connection 60, which are vertical to one another, are shown in FIGS. 2b) and 2c), wherein the section in FIG. 2b) runs vertically through the central axis and the section in FIG. 2c) runs horizontally through the central axis of the plug connection 60.

Figure 1B:
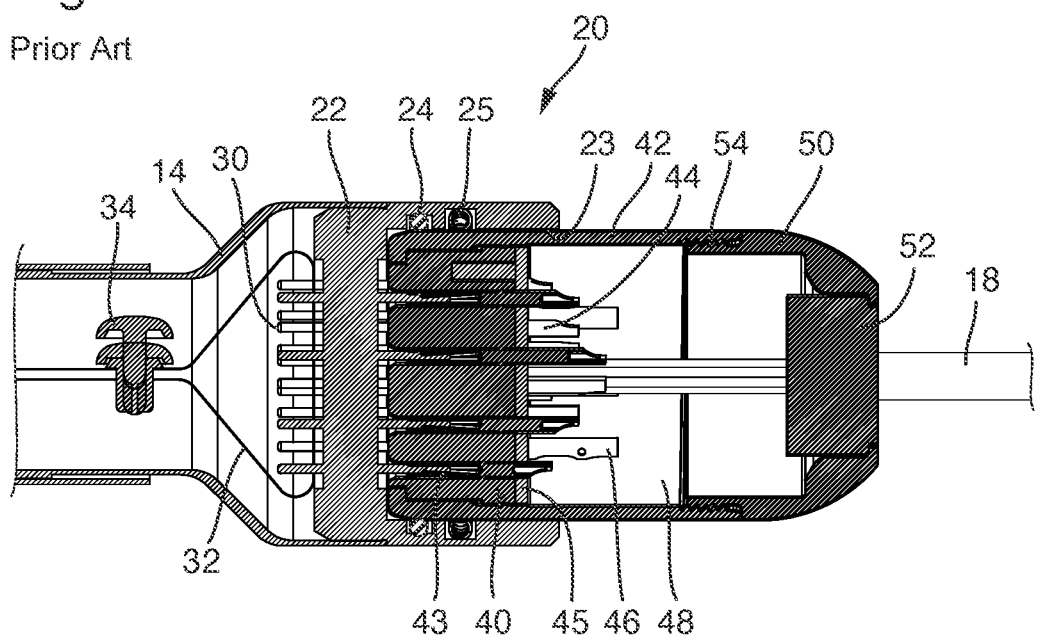
Figure 1C:
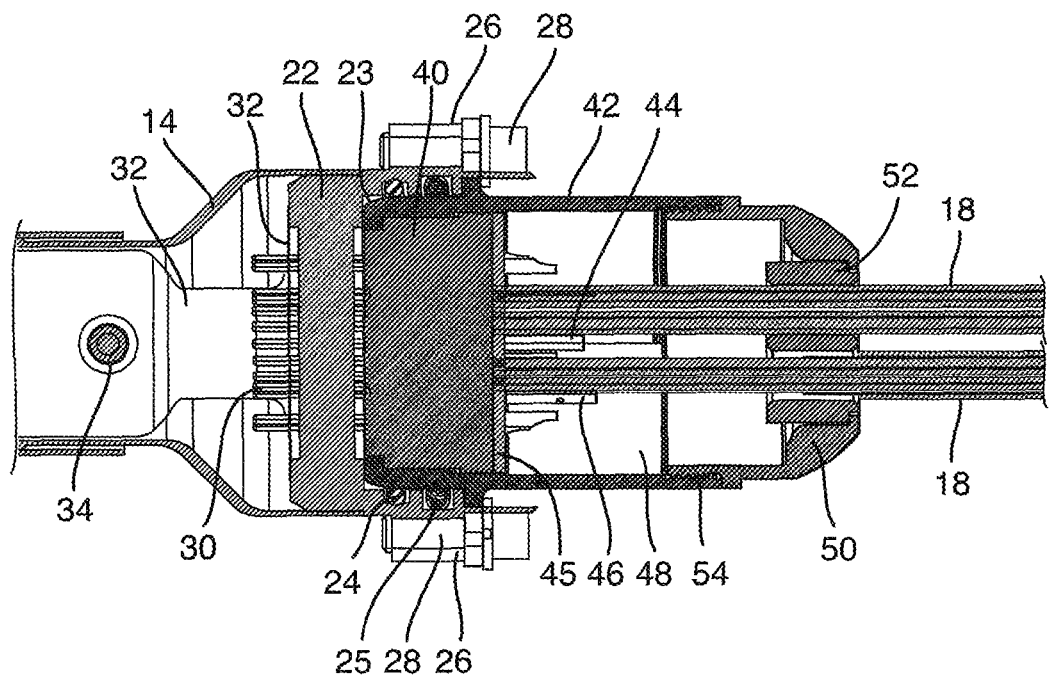

On the distal side, the plug 62 having the connection to the flexboard 72 is configured in a functionally similar manner to that in the known example from FIG. 1b). However, the plug 62 does not protrude as much in the radial direction as the plug 22 from FIG. 1b). The connector 80 is likewise configured, in its central part, in a similar manner to the connector 40 from FIG. 1b). It is, however, not covered by a cover disk 45. Instead, in the case of the connector, a connection to a flexboard 86 is achieved in a similar way to the plug 62, which flexboard likewise has a round base having the corresponding passages and solder pads for the electrical feedthroughs 84 as well as two arms which can be bent up and joined with their backs as represented in FIG. 2b). The feedthroughs 84 are, in turn, distally arranged in receptacles 83 for the feedthroughs 70 of the plug 62.

The plug 62 likewise has a connector receptacle 64 and electrical feedthroughs 70 and has a thread structure at the proximal end of its edge of the outer side, which thread structure interacts with an internal thread structure of the union nut 94. The connector housing 82 has a corresponding circumferential elevation which is entrained by the union nut 94 and is pressed onto the proximal end of the plug 62, leading to a mechanically secure and stable as well as a hermetic joining of the plug connection 60.

The connector is produced by soldering the flexboard 86 to the electrical feedthroughs 84 of the connector 80. The flexboard 86 can thus be designed such that it can be used for multiple appliances. Subsequently, the side surfaces of the flexboard 86 are bent upwards and the connector 80 is pressed into the distal connector housing 82. The round pattern of the electrical feedthroughs 84 is transformed by the flexboard 86 into a planar solder pad structure 87 which has solder pads 87' for signal lines and solder pads 87" for the sheathing or respectively shielding of the cables. The shields of the coaxial cables are no longer twisted with one another but, in common with the inner conductors, are stripped and shortened to a standard length. Thereafter, the cables 18 are soldered into the ferrule 92. The cables are subsequently soldered next to one another in the same way onto the planar solder pad structure 87 of the flexboard 86. This construction produces a much smaller jump in the transfer impedance than the solution known from the prior art according to FIG. 1b).

The connector housing 14 can be terminated by means of a ferrule 92 which fits into a proximal receptacle 89 of the connector housing, said ferrule 92 having lead-throughs 85 for the signal and supply cables. The plug 62 is inserted into the housing 14 of the distal video unit and is connected to the housing 14 such that a part 61 of the plug 62 projects proximally out of the housing 14. Thus, outer contours of the plug 62 can be used for securing, for instance by the external thread 81 for the union nut 94.

Subsequently, a lid or respectively proximal connector housing part 90, which can be constructed in one or two parts, is pushed over from the side of the ferrule 92 and pressed with the distal connector housing 82. Two grooves, which position the surfaces of the flexboard 86 centrally in the connector, are integrated into this proximal connector housing 90 which does not have a round design. In this way, no additional clip is required in order to hold the soldering surfaces centrally, and the surfaces of the flexboard 86 can be completely utilized for the routing of the conductive tracks. Subsequently, the ferrule 92 is soldered to the lid or respectively proximal connector housing 90. Since the contours are no longer round, but angular, the cable lengths can no longer be shortened by rotation during assembly. This is supported in that the ferrule 92 does not have to have a cylindrical shape. To conclude, the connector is cast through a bore until the casting compound of the casting 88 can be seen in ventilation bores. An advantage of this is that the connector is completely cast and consequently all of the mechanical loads are absorbed by the casting compound and the solder contactings are kept free of mechanical loads. The plug connection 60 is then secured with the union nut 94. This securing builds up very much less than in the case of the known plug such that the connection fits into a smaller handle and there is still space, for example, for a fiber optic plug.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

10 Video endoscope
12 Distal video unit
14 Housing
16 Proximal cable unit
18 Signal and supply cable
20 Plug connection
22 Plug having glass casting
23 Connector receptacle
24 O-ring
25 Coil spring ring
26 Eye having internally threaded bore
28 Screw having spring washer
30 Electrical feedthrough (pin)
32 Flexboard
34 Connecting element
40 Connector
42 Connector housing
43 Receptacle
44 Electrical feedthrough (pin)
45 Cover disk
46 Solder adapter
48 Casting
50 Lid
52 Ferrule
54 Screw connection
60 Plug connection
61 Part of plug extending proximally from housing
62 Plug having glass casting
64 Connector receptacle 70 Electrical feedthrough (pin)
72 Flexboard
79 Termination surfaces
80 Connector
81 External threads
82 Distal connector housing part
83 Receptacle
84 Electrical feedthrough (pin)
85 Lead-through
86 Flexboard
87 Solder pad structure
87' Solder pad for signal line
87" Solder pad for sheathing (compound)
88 Casting
89 Proximal receptacle
90 Proximal connector housing part
92 Ferrule
94 Union nut

What is claimed is:

1. A plug connection for a video endoscope for producing a signal connection between a distal video unit and a proximal cable unit of the video endoscope, the plug connection comprising:
    a plug; and
    a complementary connector configured to be inserted into the plug in order to produce and interrupt the signal connection,
    wherein the plug is formed as a glass cast part and is arranged at a proximal end of the distal video unit;
    the connector is arranged at a distal end of the proximal cable unit;
    the plug is connected on its outer side to a housing of the distal video unit, the plug has a plurality of electrical feedthroughs, the plug is connected in an electrically conducting manner on a distal side to a first flexboard in the distal video unit and the plug has on its proximal side a connector receptacle configured as a recess for the connector;
    the connector is enclosed in a connector housing which is formed on its outer side to fit the connector receptacle of the plug in order to be received in the connector receptacle of the plug by one or more of a form-fit and a force-fit;
    the connector has a plurality of electrical feedthroughs which are arranged in accordance with an arrangement of the electrical feedthroughs of the plug;
    the electrical feedthroughs of the connector are connected proximally to a second flexboard which has a planar solder pad structure having solder pads, to which signal and connecting cables are soldered; and
    the connector housing is completely filled with a casting.

2. The plug connection according to claim 1, wherein the plug and the connector housing have structures on their outer sides, the structures including external threads and termination surfaces, which cause the plug connection to be pressed on and fixed by screwing on a union nut.

3. The plug connection according to claim 1, wherein the connector housing has a smaller cross-sectional area in a first region of the second flexboard than in a second region of the connector.

4. The plug connection according to claim 1, wherein the connector receptacle and the connector housing have mutually complementary structures in order to correctly align the connector and the plug with respect to one another.

5. The plug connection according to claim 1, wherein the connector housing is terminated by a ferrule which fits into a proximal receptacle of the connector housing, the ferrule having lead-throughs for the signal and connecting cables, and the signal and connecting cables are soldered into the ferrule.

6. The plug connection according to claim 5, wherein the ferrule and the proximal receptacle of the connector housing have shapes which match one another, and prevent a rotation of the ferrule in the proximal receptacle of the connector housing.

7. The plug connection according to claim 5, wherein the connector housing is configured in two parts, wherein the connector is fitted into a distal connector housing part and the ferrule is fitted into a proximal connector housing part.

8. A video endoscope comprising:
    the distal video unit;
    the proximal cable unit; and
    the plug connection according to claim 1 for producing the signal connection between the distal video unit and the proximal cable unit.

9. A method for producing the plug connection and the signal connection between the distal video unit and the proximal cable unit of the video endoscope according to claim 8, the method comprising:
    soldering the first flexboard to the electrical feedthroughs of the connector on a proximal side of the connector,
    bending side surfaces of the second flexboard proximally and pressing the connector into the connector housing,
    soldering the signal and connecting cables to the solder pads of the planar solder pad structure of the second flexboard,
    soldering the signal and connecting cables into the ferrule before or after soldering to the planar solder pad structure,
    closing the connector housing,
    soldering the ferrule to the connector housing; and
    completely filling the connector housing with the casting.

10. The method according to claim 9, further comprising:
    at the proximal end of the distal video unit, connecting the electrical feedthroughs of the plug configured as a glass cast part to contact surfaces of the first flexboard, and
    inserting and connecting the plug into the housing of the distal video unit such that a part of the plug projects proximally out of the housing.

11. The method according to claim 9, wherein the closing comprises pushing a proximal connector housing part onto or into a distal connector housing part and pressing with the distal connector housing part.

12. The method according to claim 9, securing the plug connection with a union nut.

* * * * *